United States Patent
Summers

[11] Patent Number: 6,080,191
[45] Date of Patent: *Jun. 27, 2000

[54] METHOD FOR MAKING A STENT

[75] Inventor: David Paul Summers, Montgomery, Tex.

[73] Assignee: American BioMed, Inc., The Woodlands, Tex.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/782,407

[22] Filed: Jan. 14, 1997

Related U.S. Application Data

[63] Continuation of application No. 08/367,239, Dec. 16, 1994, Pat. No. 5,607,445, which is a continuation-in-part of application No. 07/900,896, Jun. 18, 1992, Pat. No. 5,342,387.

[30] Foreign Application Priority Data

Jun. 16, 1993 [WO] WIPO ............ PCT/US93/05823

[51] Int. Cl.⁷ .................................................. A61M 29/02
[52] U.S. Cl. ...................... 623/1.22; 623/1.16; 72/135
[58] Field of Search .................... 606/198, 191; 623/901, 1.17, 1.22, 1.16, 1.15; 72/135, 203, 365.2

[56] References Cited

U.S. PATENT DOCUMENTS

| | | | |
|---|---|---|---|
| 4,969,458 | 11/1990 | Wiktor | 606/194 |
| 5,161,547 | 11/1992 | Tower | 128/898 |
| 5,370,683 | 12/1994 | Fontaine | 606/198 X |
| 5,540,713 | 7/1996 | Schnepp-pesch et al. | 606/198 |
| 5,632,771 | 5/1997 | Boatman et al. | 606/198 X |

*Primary Examiner*—Michael H. Thaler
*Attorney, Agent, or Firm*—Conley, Rose & Tayon, P.C.

[57] ABSTRACT

A stent comprising a coil including a plurality of arcuate sections that alternate directions around a central axis, each arcuate section including a pair of curved turns joined by a cusp, and the cusps of adjacent arcuate sections intermeshing and defining at least one region of overlap, which in turn describes a helix around and along the length of the coil. In the preferred embodiment, there are two regions of overlap, which together describe a double helix. In another preferred embodiment, the stent is bifurcated so as to support a branched vessel or the like.

A method for forming a stent, including the steps of providing a flat sheet of material, chemically etching said sheet to form a blank, and forming said blank into a cylindrical coil. The coiling step is preferably carried out on a plurality of rollers.

10 Claims, 15 Drawing Sheets

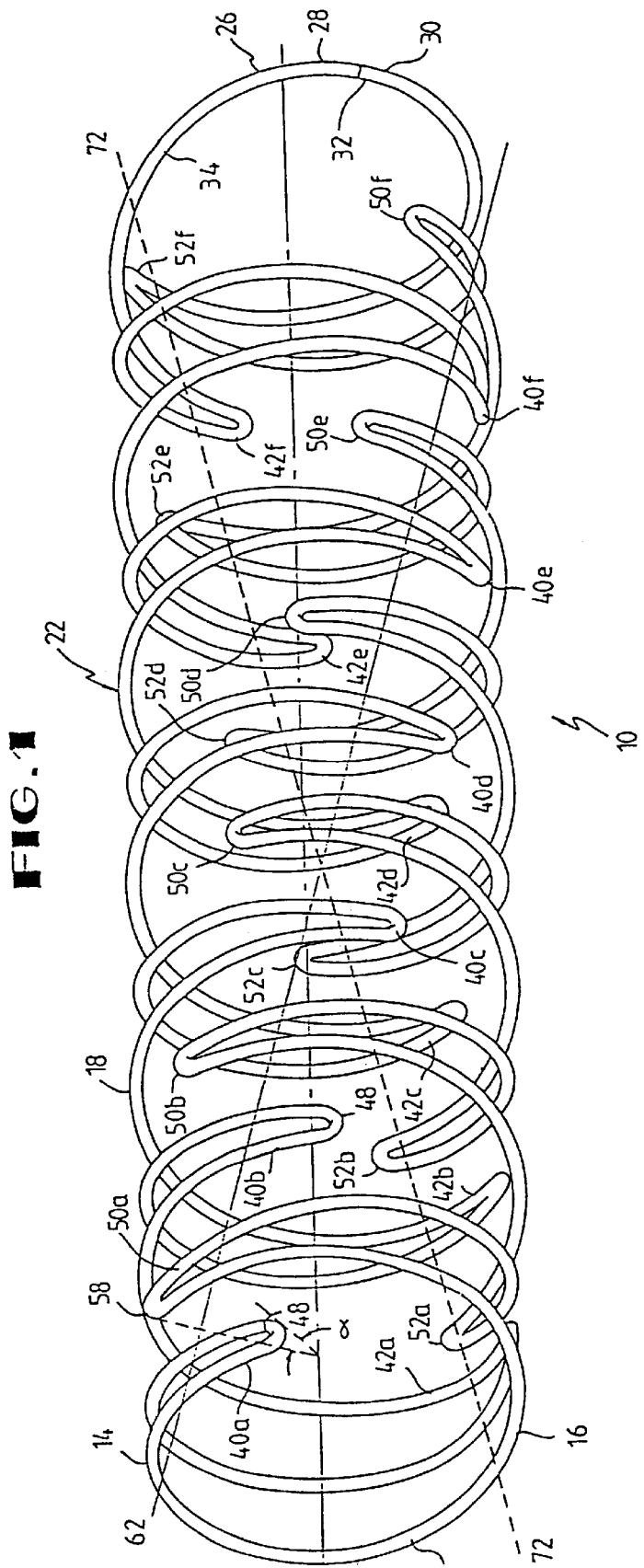

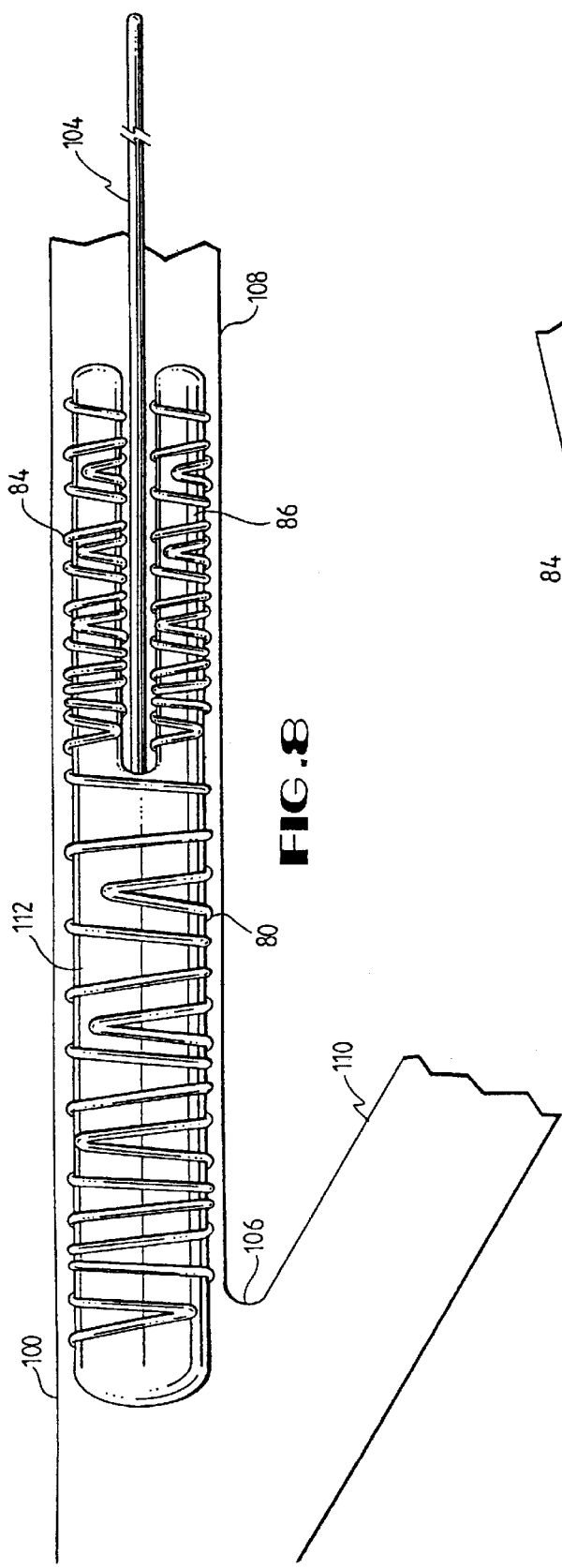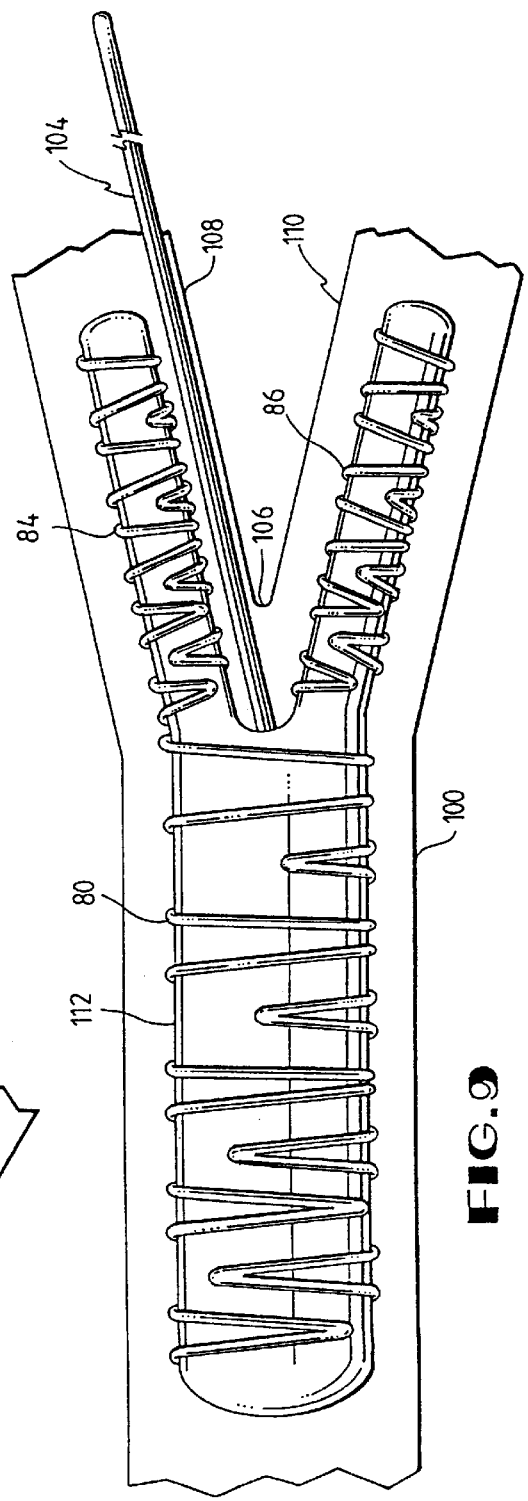

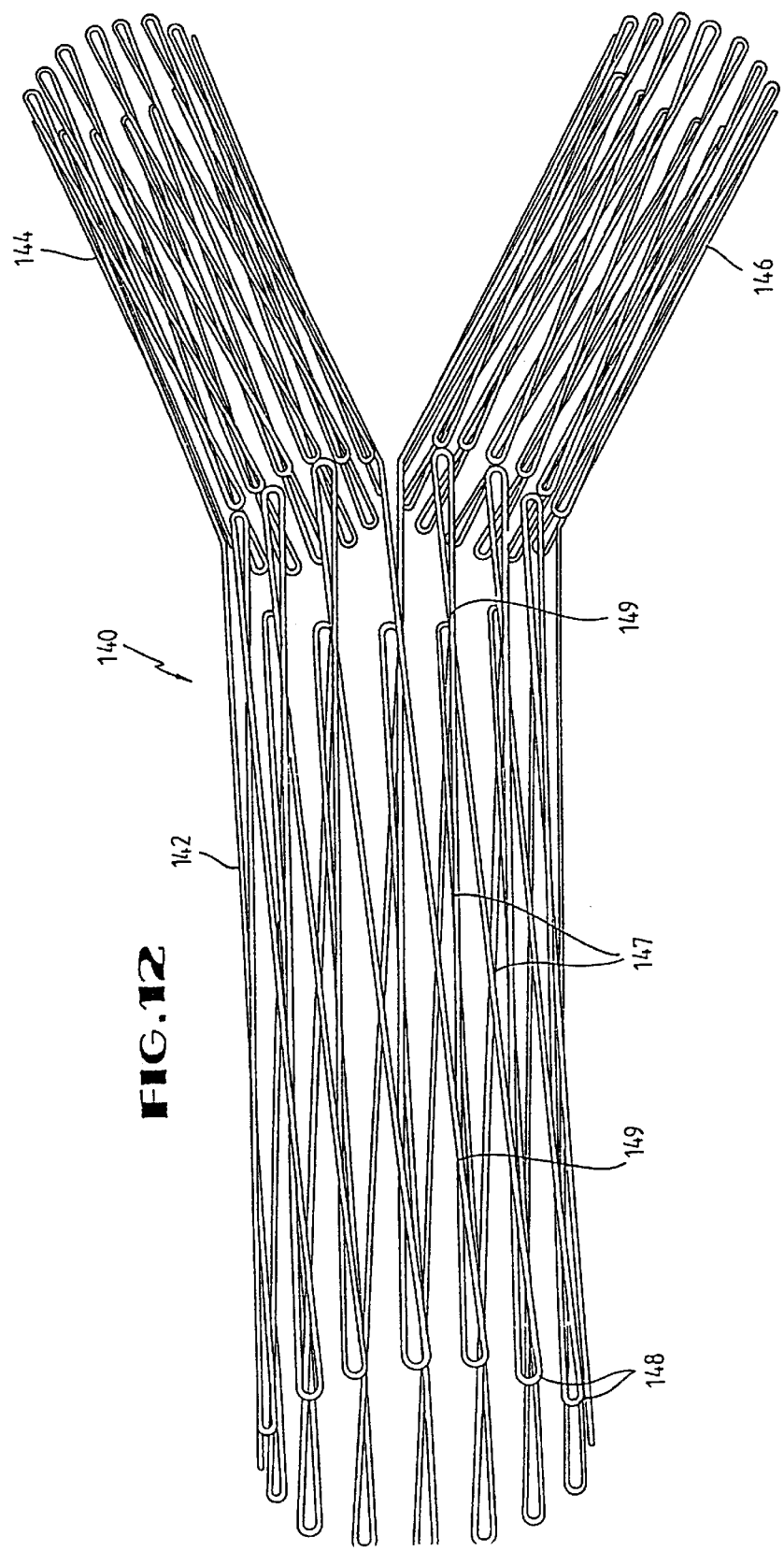

METHOD FOR MAKING A STENT

This is a continuation of co-pending application(s) Ser. No. 08/367,239 filed on Dec. 16, 1994, now U.S. Pat. No. 5,607,445 which is the national phase of International Application PCT/US93/05823 filed on Jun. 16, 1993 which designated the U.S. and which is a continuation-in-part of Ser. No. 07/900,896 filed on Jun. 18, 1992 now U.S. Pat. No. 5,342,387.

TECHNICAL FIELD OF THE INVENTION

The present invention relates to supports for collapsed or occluded blood vessels, and more particularly, to a coiled wire stent for insertion and expansion in a collapsed or occluded blood vessel. Still more particularly, the present invention relates to a coiled, bifurcated stent which supports a Y-shaped juncture of two blood vessels.

The present invention further relates to methods and apparatus for manufacturing artificial supports for blood vessels and more particularly, to methods for making a wire coil having certain desired properties. Still more particularly, the present invention discloses methods and apparatus for preparing a continuous loop and forming the loop into a cylindrical shape having a desired configuration.

BACKGROUND OF THE INVENTION

A typical wire stent for insertion and expansion in a collapsed or occluded blood vessel is shown in U.S. Pat. No. 4,800,882 and includes a coiled wire having a plurality of curved sections that are formed into a generally circular configuration. Adjacent curved sections are joined by a bend so that a series of alternating opposing loops are formed. The stent has a cylindrical shape with a longitudinal opening through which a folded balloon catheter is inserted. The opposing loops are tightly contracted about the catheter so that the cylindrical shape has an overlapping region in which portions of adjacent loops circumferentially overlap. The loops are arranged so that when the balloon catheter is inflated, adjacent loops diverge circumferentially relative to each other, thereby decreasing the width of the overlapping region while increasing the diameter of the cylindrical shape. As the diameter of the cylindrical stent increases, the stent engages the inner surface of the blood vessel.

In operation, the stent is deployed at its desired position within the vessel in its collapsed state, by threading the balloon catheter tip the vessel from an incision some distance away, and then expanded to its expanded state, for supportive engagement with the interior of the vessel wall.

The prior art stents have several deficiencies. As shown in FIG. 7 of U.S. Pat. No. 4,800,882, the alternating bends are aligned in relation to the longitudinal axis of the stent such that upon expansion of the stent as shown in FIG. 8, the opposing loops may be expanded such that a longitudinal gap appears between the opposing bends of the loops, leaving a longitudinal unsupported area along the occluded blood vessel. Such an unsupported area is undesirable. Further, when it is desired to support a branched section of a blood vessel without obstructing the passageway of the vessel, it is necessary to utilize several conventional stents to support the main vessel and the adjacent two branch vessels. Deployment of multiple stents requires an extended medical procedure, and may produce unsatisfactory results if any of the stents migrates away from the juncture, leaving one leg of the Y-shaped juncture of the vessels unsupported. Additionally, the stents of the prior art often require the application of heat, torsional force, or a shortening in length in order to attain their expanded state.

Alternatively, stents having no longitudinal gap may be comprise spiral coils, or other configurations that are radially expandable and provide the desired circumferential support for a collapsed vessel.

Because of the asymmetrical nature of many of the desired coil configurations, standard manufacturing methods are inapplicable. Thus, stents such as that disclosed in U.S. Pat. No. 4,800,882, involve a high degree of labor to produce. The present invention discloses means and apparatus for producing a desired stent quickly and easily.

The present invention overcomes the deficiencies of the prior art.

SUMMARY OF THE INVENTION

The stent of the present invention comprises a coil including a plurality of arcuate sections that alternate clockwise and counterclockwise directions around a central longitudinal axis. Each arcuate section includes a pair of curved turns joined by a cusp. The cusps of adjacent arcuate sections intermesh, thereby defining at least one region of overlap, which in turn describes a helix around and along the length of the coil. In the preferred embodiment, there are two regions of overlap, which together form a double helix.

The present invention further discloses a Y-shaped, bifurcated stent. The bifurcated stent comprises three coils, each constructed according to a preferred coil pattern, joined so as to form an unobstructed support for a branched vessel.

The stent of the present invention is radially expandable without the use of heat, torsional forces, or shortening of the stent, and is constructed to provide a region of enhanced support which wraps helically around the stent. The branched stent fills the need for a reliable device which is simple to install and effectively supports a branched blood vessel.

The present invention further discloses a double-spiral stent that may comprise either a single coil or a bifurcated coil, and a rib-cage type stent that includes a longitudinal spine supporting a plurality of looped ribs thereon.

Also disclosed is a method for making the foregoing stents that is rapid, repeatable and economical. The method of the present invention is not labor intensive and is capable of producing even stents that do not have a linear axis of symmetry. The present method includes creating a continuous loop, or blank, by photoetching a sheet of material. The blank produced by the photoetching technique has no ends or joints and is therefore superior for internal applications because the likelihood of a puncture or other damage is minimized.

The present method further includes rolling the continuous blank between a series of rollers, to form a cylindrical coil. According to the present invention, the precise configuration of the coil is determined by the shape of the blank that is rolled. Thus, single-helix, double-helix and spiral configured stents may be constructed by rolling according to the present invention.

Alternatively, a method for constructing the desired coil shape by hand is disclosed. The manual method comprises forming each loop of the coil around a mandril by individually pulling the cusps of the coil into place. This manual method may of course be automated to increase speed and efficiency of production.

Other objects and advantages of the present invention will appear from the following description.

BRIEF DESCRIPTION OF THE DRAWINGS

For a detailed description of a preferred embodiment of the invention, reference will now be made to the accompanying drawings wherein:

FIG. 1 is a perspective view of a double-helix nonbifurcated stent according to the present invention.

FIG. 8 is a side elevational view of the stent of FIG. 6 in a collapsed state, mounted on a balloon catheter within a blood vessel.

FIG. 9 is a side elevational view of the stent of FIG. 6 deployed within a bifurcated vessel and partially expanded.

FIG. 12 is a perspective view of a bifurcated zig-zag stent according to the present invention.

DETAILED DESCRIPTION OF A PREFERRED EMBODIMENT

Double Helix Stent

Figure 2:
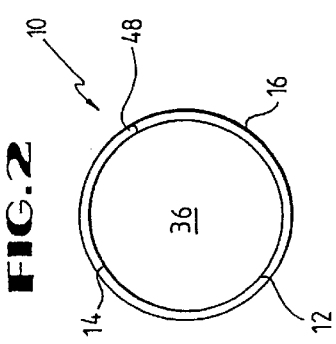
FIG. 2 is an end view of the double-helix nonbifurcated stent of FIG. 1.

Referring initially to FIGS. 1 and 2, there is shown a preferred embodiment of a stent 10 according to the present invention. Stent 10 is made of a single length of wire having a mid-point at 12 forming two wire legs 14, 16 of approximately equal length. Legs 14, 16 are bent into a double-helix coil 22 as shown, forming individual spiral wire shell halves 18, 20 respectively. One end 24 of coil 22 includes mid-point 12, and the other end 26 of coil 22 includes the terminal ends 28, 30 of wire legs 14, 16. Terminal ends 28, 30 are connected at juncture 32 on coil end 26, such as by soldering or the like. Upon the joining of terminal ends 28, 30, coil 22 effectively consists of a single continuous wire 34. The two wire shell halves 18, 20 are curved, as shown in the end view of FIG. 2, so that stent 10 is generally cylindrical in shape with a generally circular opening 36 formed therein. Stent 10 is shown having a central longitudinal axis 38.

Figure 3:
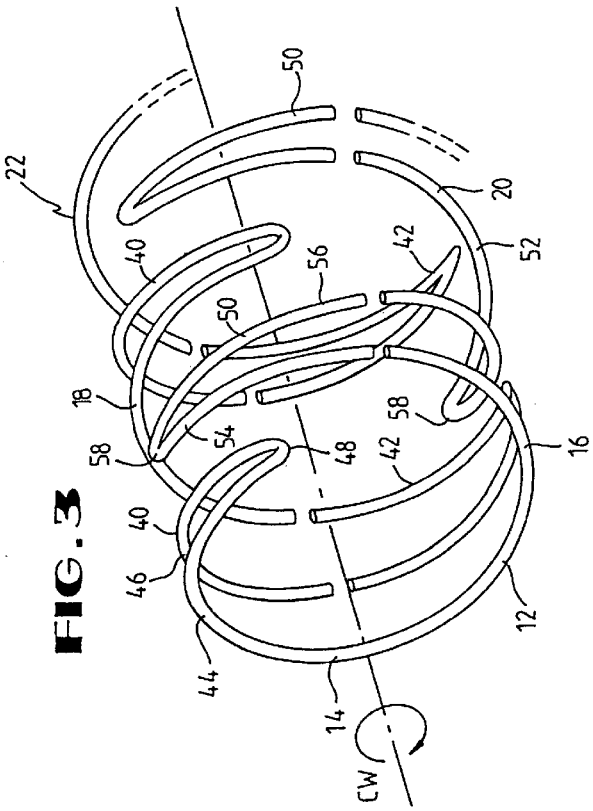
FIG. 3 is an enlarged view of two full loops of the double-helix stent of FIG. 1.
Figure 4:
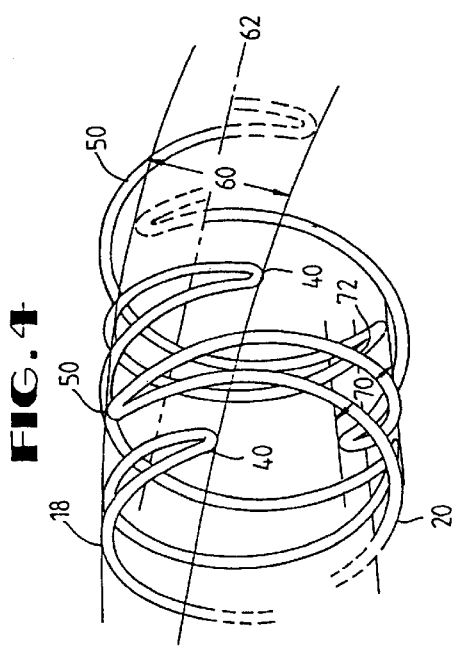
FIG. 4 is a close-up view of two full loops of the double-helix stent of FIG. 1.

Referring now to FIGS. 1, 3, and 4, each individual spiral wire shell half 18, 20 includes a series of alternating clockwise and counterclockwise arcuate sections. For purposes of description, the arcuate sections have been severed in FIG. 3 to better illustrate such sections. The clockwise direction relative to the axis 38 has been arbitrarily selected and is indicated by the arrow CW. Wire shell half 18 includes alternating clockwise and counterclockwise arcuate sections 40, 42, respectively, and opposed wire shell half 20 includes alternating counterclockwise and clockwise arcuate sections 50, 52, respectively. Clockwise arcuate section 40 is typical of the other arcuate sections and includes two adjacent curved turns 44, 46 of wire joined by a bend or cusp 48. Likewise, counterclockwise arcuate section 50 of shell half 20 includes two adjacent curved turns 54, 56 joined by a cusp 58.

As best seen in FIG. 1, wire leg 14 forms shell half 18, comprising clockwise arcuate sections 40a, 40b, 40c, etc., with cusps 48 pointing in the clockwise direction and counterclockwise arcuate sections 42a, 42b, 42c, etc., with cusps 48 pointing in the opposite counterclockwise direction. Likewise, wire leg 16 forms shell half 20 comprising counterclockwise arcuate sections 50a, 50b, 50c, etc. with cusps 58 and clockwise arcuate sections 52a, 52b, 52c, etc. with cusps 58. The clockwise arcuate sections 40 of shell half 18 are in phase with the counterclockwise arcuate sections 50 of shell half 20 so that the clockwise arcuate sections 40 of half 18 intermesh and extend between counterclockwise arcuate sections 50 of half 20. The same is true for counterclockwise arcuate sections 42 of half 18 and clockwise arcuate sections 52 of half 20.

Referring now to FIG. 4, the intermeshing of arcuate sections 40, 50 and 42, 52 creates two regions of overlap in coil 22. Clockwise arcuate sections 40 and counterclockwise arcuate sections 50 create a first overlap region 60 and counterclockwise arcuate sections 42 and clockwise arcuate sections 52 create a second overlap region 70. Regions of overlap 60, 70 have diametrically opposed centerlines 62, 72, respectively.

Referring now to FIGS. 1 and 4, the extent of the regions of overlap 60, 70 will vary with the size of the blood vessel in which the stent 10 is deployed. The extent of the region of overlap 60, 70 is maximized in the contracted position of the stent 10 and is minimized in the expanded position of the stent 10. The intermeshing of adjacent arcuate sections 40, 50 and 42, 52 defines an angle a at axis 38, shown in FIG. 1. Preferably, in the contracted position, α is at least five longitudinal degrees. In the Figures, an intermeshing of only a few longitudinal degrees is shown, but it will be understood that the degree of intermeshing can be increased without departing from the spirit of the invention and is actually increased when the stent is used. Cusps 48, 58 of arcuate sections 40, 42, 50, 52 shift circumferentially with each turn. In this manner, regions of overlap 60, 70 describe a double-helix around coil 22, best demonstrated by reference centerlines 62, 72, shown in FIG. 1. The advantages of this construction will become apparent from the discussion below.

Preferably, stent 10 is constructed of wire, although any suitable material may be substituted. The wire comprising stent 10 is malleable, preferably from the group consisting of annealed stainless steel, tungsten and platinum. This malleable material must be sufficiently deformable to allow shell halves 18, 20 to expand radially when radially outward pressure is applied by the inflation of the membrane that comprises the standard balloon catheter. Because the stent material deforms plastically, rather than elastically, the stent 10 retains the enlarged diameter after the balloon is deflated.

The material has sufficient strength and stiffness, however, to avoid the stent 10 being displaced during insertion and to avoid the adjacent arcuate sections 40, 50 and 42, 52 being forced into an overlying relation. Further, the stent 10 has sufficient strength and stiffness to allow it to maintain its position in the vessel passageway and to resist being dislodged after the catheter has been deployed. One example of a suitable wire has an outer diameter of 0.018 inches and is stainless steel AISI 315 alloy. Alternately, the stent 10 of the present invention can be constructed of a memory metal, such as Nitinol, that resumes a particular original shape, following deformation, when heat is applied.

In a preferred embodiment, the surface of the stent is coated with a biocompatible substance, preferably a biolized collagen/gelatin compound such as those discussed in *Characterization of Rehydrated Gelatin Gels*, Emoto. et al., *Artificial Organs*, 15(1):29–34, 1991 and incorporated herein by reference. The coating serves to increase biocompatibility of the stent and aid in blood flow around the device. The coating is a 5% glutaraldehyde cross-linked dried gelatin coating which can be applied to a texturized surface, dehydrated, sterilized, and stored dry. This type of gel, when applied as a film, provides a smooth, biochemically stable protein coating with non-pseudointima properties, very little platelet adhesion, and high blood compatibility.

To deploy a stent such as the stent 10 of FIG. 1 in a blood vessel, the stent is radially contracted or compressed until it assumes a outer diameter which is calibrated to allow insertion into a particular vessel passageway. Typically, this means an outer diameter on the order of 3 millimeters. With regard to stent 10, as the stent is compressed, regions of overlap 60, 70 widen and the cusps 48, 58 are forced into deeper intermeshing relationship. The stent 10 in its contracted state is threaded onto a balloon catheter (not shown) prior to deployment in the vessel. The compressed stent 10 and catheter are inserted at an incision in the vessel and threaded up the vessel on a wire guide to the place of deployment. At that point, pressure is applied to the balloon to expand it within the stent. As the balloon is inflated, the clockwise and counter-clockwise arcuate sections 40, 50 and 42, 52 expand radially, reducing the width of overlap regions 60, 70 until the desired circumference is attained. Thus, the effective diameter of stent 10 is increased without thermal expansion, application of torsional forces to the stent, or a reduction in overall length of the stent.

Single Helix Stent

Figure 5:
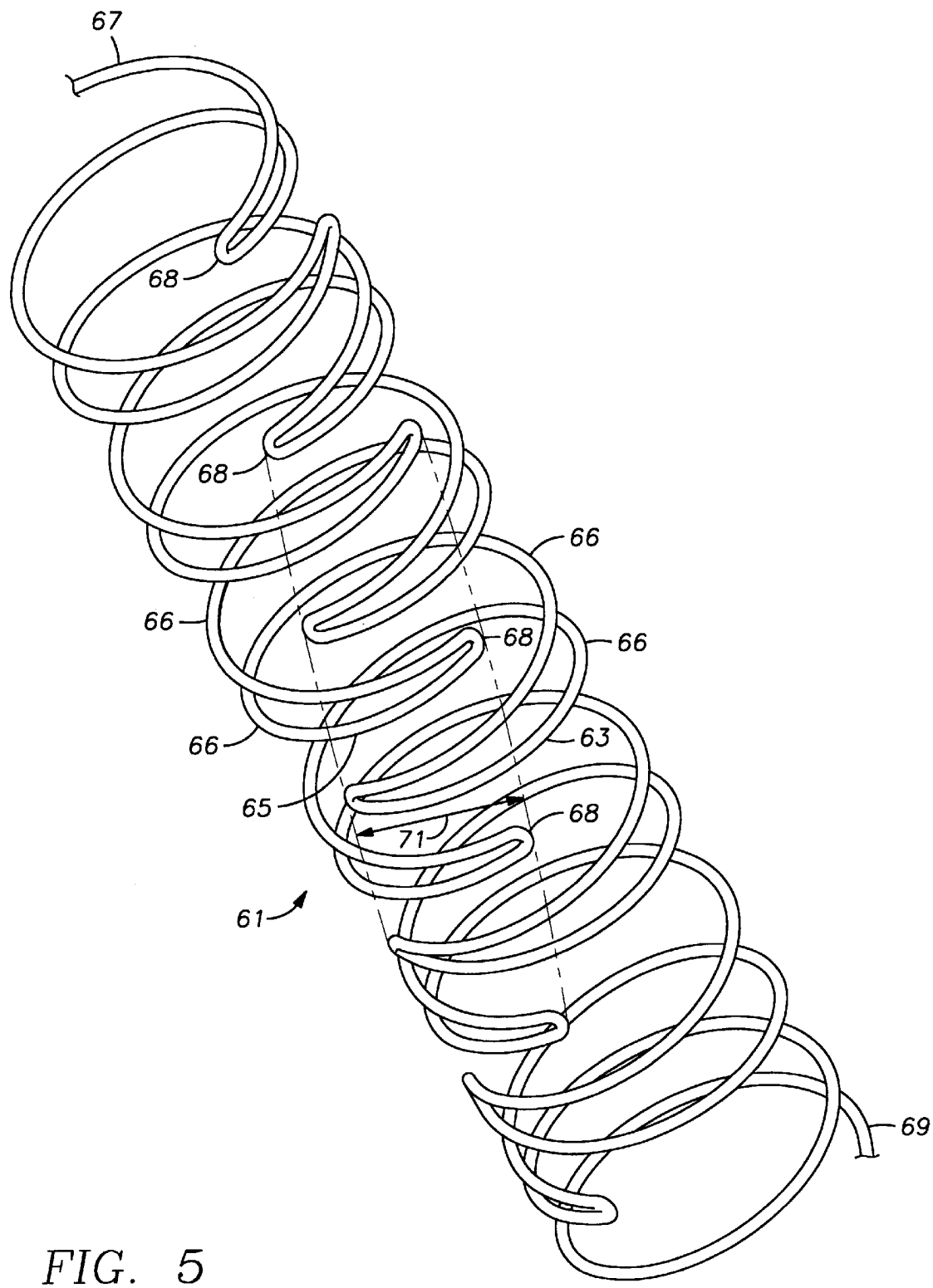
FIG. 5 is a perspective view of a single-helix nonbifurcated stent.

Referring now to FIG. 5, there is shown an alternate nonbifurcated stent 61 comprising a single helix coil 64. According to this embodiment, a wire is bent into a series of alternating clockwise and counterclockwise arcuate sections 63, 65, formed by turns 66 and cusps 68, such that one region of overlap 71 is formed. The ends 67, 69 of the wire are located at opposite ends of coil 64. As described above with regard to stent 10, arcuate sections 63, 65 are constructed so that region of overlap 71 shifts longitudinally with each successive turn 66 and forms a spiral around coil 64. Because there is only one region of overlap, 71, coil 64 is referred to as a single-helix coil. Stent 61 can be deployed in the manner discussed above with regard to stent 10.

Figure 6:
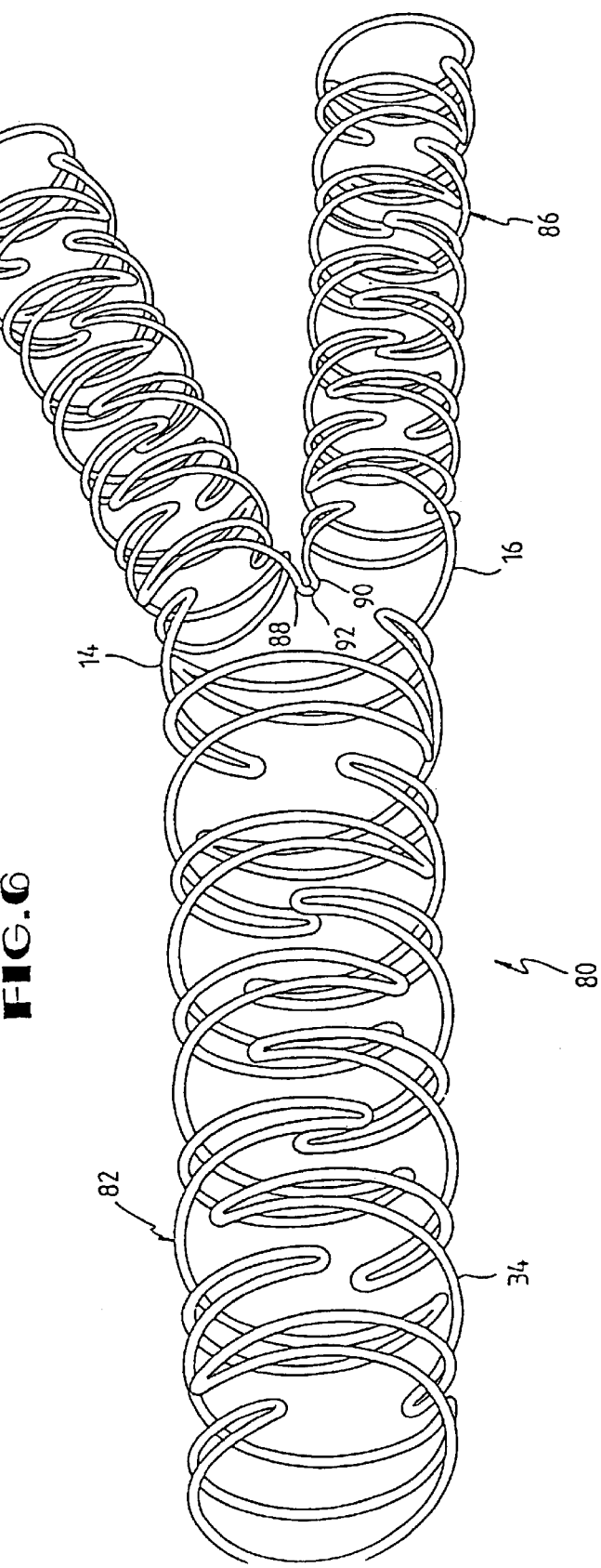
FIG. 6 is a perspective view of a double-helix bifurcated stent according to the present invention.

Referring now to FIG. 6, there is shown a preferred bifurcated stent 80 according to the present invention. Bifurcated stent 80 includes a major coil 82 and two minor coils 84, 86. In practice, major coil 82 may be placed, for example, in the aortic vessel and minor coils 84, 86 in the iliac vessels. As with stent 10, bifurcated stent 80 comprises a single continuous wire 34, and each of coils 82, 84, 86 comprises a part of the wire 34. Major coil 82 has the same double helix pattern as coil 22 of stent 10, with the exception that wire legs 14, 16 are extended to form minor coils 84, 86, respectively, which are also coiled in the double helix pattern of coil 22. As in coil 22, the terminal ends 88, 90 of wire legs 14, 16 are joined at a juncture 92. Hence, a single wire loop is able to define and flexibly support a branched vessel without obstructing flow therethrough.

Figure 7:
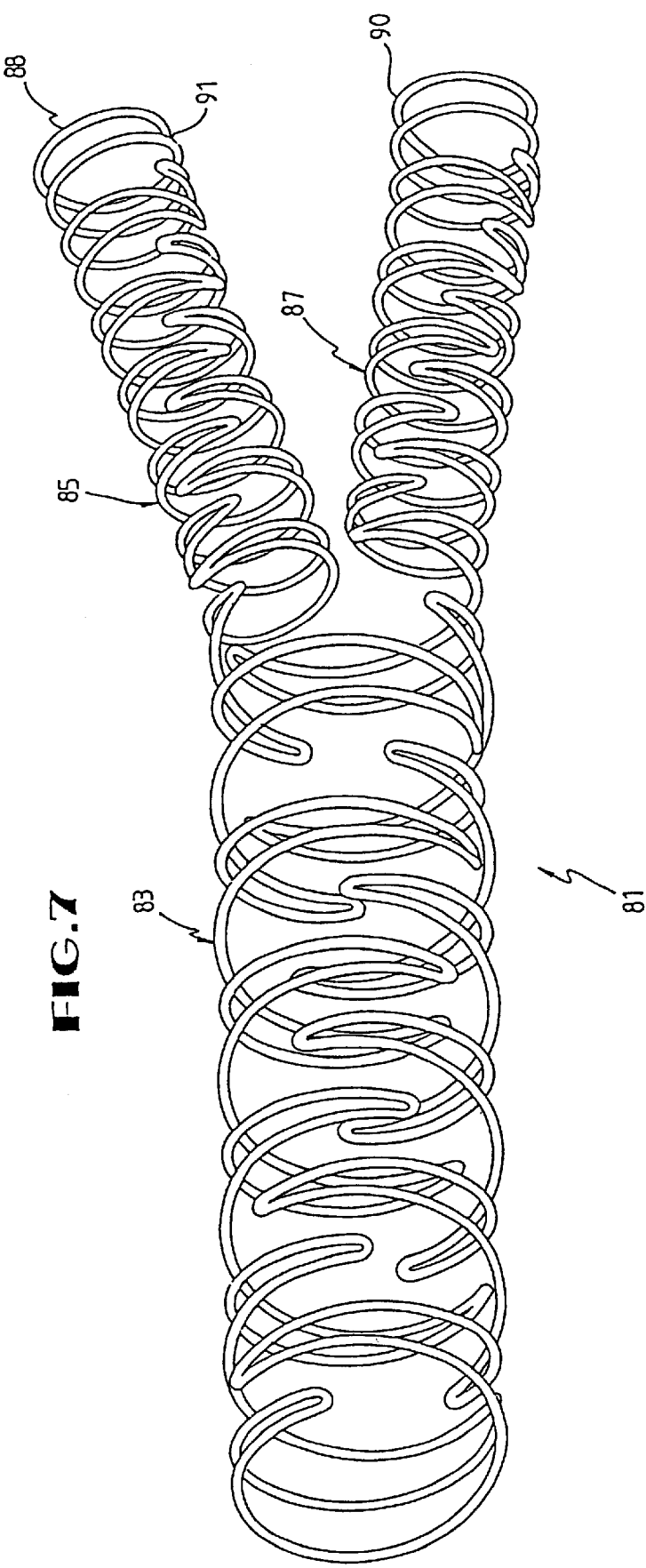
FIG. 7 is a perspective view of a bifurcated stent in which the major coil is a double-helix and the two minor coils are single-helix.

Referring now to FIG. 7, an alternate bifurcated stent 81 comprises one major coil 83 constructed in the manner of double-helix coil 22 of stent 10 shown in FIG. 1, and two minor coils 85, 87 constructed in the manner of single-helix coil 64 of stent 61 shown in FIG. 5. As with bifurcated stent 80, bifurcated stent 81 can be constructed from a single piece of wire. In stent 81, wire legs 14, 16 terminate at ends 88, 90, which may be joined to coils 85, 87, as shown at 91, individually formed into loops (not shown), or otherwise prevented from puncturing the vessel wall.

Deployment of a bifurcated stent is shown in FIGS. 8 and 9, using the stent 80 shown in FIG. 6. Stent 80, in a contracted state on balloon catheter 112, is threaded up one of the iliac vessels 108, 110 from an incision in the leg, as shown in FIG. 8. When it reaches the juncture 106 of vessels 108, 110, the stent 80 is pushed up into the aortic vessel 100 by a guide wire 104, until one of the minor coils 84, 86 of the stent 80 is clear of the juncture 106. Then the stent 80, still in a compressed state, is backed down the iliac vessel 108 until it is in its proper position for expansion. FIG. 9 shows stent 80 in position for deployment within the vessel juncture 106 and partially expanded. Bifurcated stents of the present invention having a variety of coil patterns may be deployed in the manner described above with respect to stent 80.

As shown in FIGS. 8 and 9, a tri-wing balloon 112 may be used to inflate stent 80, so that uniform pressure is applied to each coil of stent 80 and the coils expand simultaneously. The balloon material is flexible, so that, once deflated, it may be easily removed through any opening in the stent 80. Preferably, it is removed through an opening where the aortic section branches to form the iliac sections, or through the end of one of the iliac sections.

Cross-Over Stents

Figure 10:
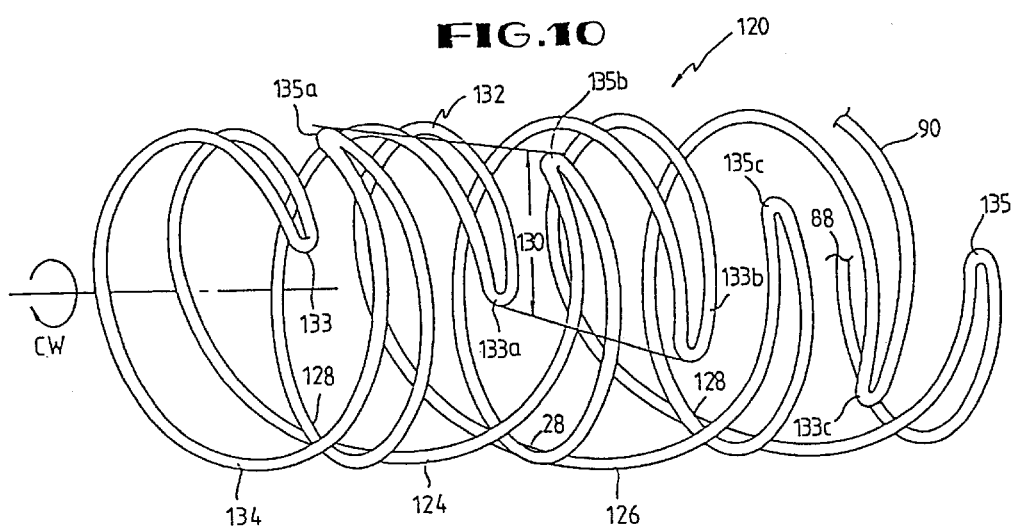
FIG. 10 is a perspective view of a first nonbifurcated cross-over stent.

Referring now to FIG. 10, an additional single-helix, nonbifurcated coil 120, is shown. In coil 120, both wire ends 88, 90 are at one end of the coil 120, and one region of overlap 130 is formed. In alternate embodiments of coil 120 (not shown), wire ends 88, 90 may be joined as at 32 in FIG. 1, formed into loops, or extended to form integral adjacent minor coils. Region of overlap 130 describes a helix around coil 120, as discussed above with respect to coil 22. Unlike coil 22, however, where the material forms two opposing individual shell halves that do not cross, the material of coil 120 forms two generally cylindrical legs 124, 126, each comprising of a series of alternating clockwise and counterclockwise sections 132, 134 having clockwise and counterclockwise cusps 133, 135, respectively. Each leg 124, 126 has its own region of overlap, and legs 124, 126 are intermeshed so that the regions of overlap coincide. When intermeshed, legs 124, 126 cross each other at a series of cross-overs 128. For this reason, coils such as coil 120 are hereinafter referred to as cross-over coils. It should be noted that in coil 120 clockwise cusps 133 and counterclockwise cusps 135 alternate along region of overlap 130.

Coil 120 provides a radially expandable coil with an asymmetrical region of overlap. The fact that both wire ends 88, 90 are at one end of coil 120 makes coil 120 suitable for the construction of either a closed loop, nonbifurcated stent or a bifurcated stent in which the minor coils are formed from, and are therefore integral with, ends 88 and 90.

Figure 11:
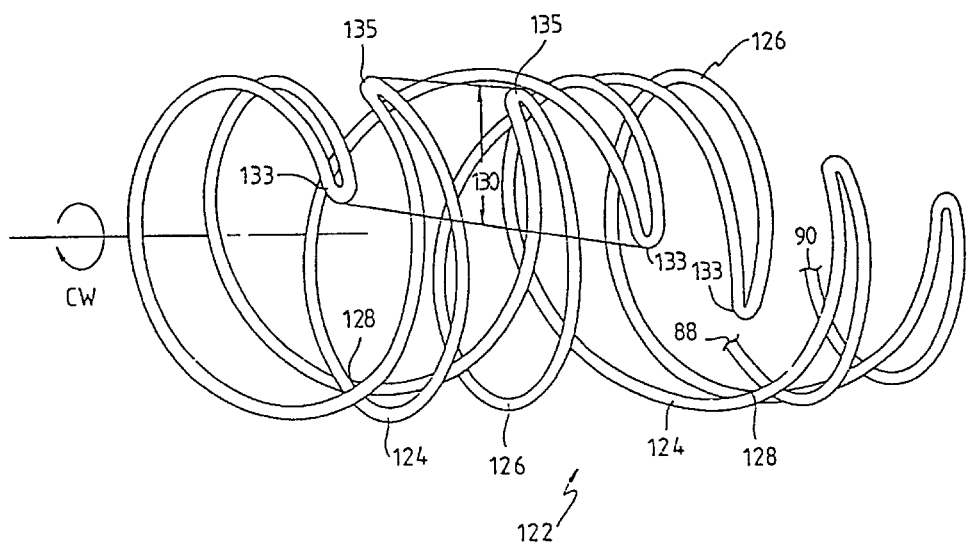
FIG. 11 is a perspective view of a second nonbifurcated cross-over stent.

Referring now to FIG. 11, an alternate single-helix, cross-over, nonbifurcated coil 120, is shown. In coil 122, as in coil 120, both wire ends 88, 90 are at one end of the coil 122, and one region of overlap 130 is formed. Region of overlap 130 describes a helix around coil 122, as discussed above with respect to coil 120. As in coil 120, the material of coil 122 forms two generally cylindrical legs 124, 126, each comprising of a series of alternating clockwise and counter-clockwise sections 132, 134 having clockwise and counter-clockwise cusps 133, 135, respectively. Each leg 124, 126 has its own region of overlap, and legs 124, 126-are intermeshed so that the regions of overlap coincide. When intermeshed, legs 124, 126 cross each other at a series of cross-overs 128. Wire ends 88, 90 of coil 122 may be treated in the same manner as discussed above with regard to coil 120.

In coil 122, however, unlike coil 120, a pair of clockwise cusps 133 is followed by a pair of counterclockwise cusps 135 etc., defining region of overlap 130 in a manner different from coil 120. The difference arises in the pitch of the turns of each leg. In coil 120, the turns have an uneven pitch, in that one leg 126 forms a first pair of adjacent cusps 135a, 133a and then passes behind the other leg 124, which forms the next pair of adjacent cusps 135b, 133b, and so on. In coil 122, the turns of each leg have a regular pitch, but do not form the alternating clockwise. counterclockwise pattern of cusps at region of overlap 130.

Zig-Zag Stent

In another alternate embodiment, shown in FIG. 12, a bifurcated stent 140 comprises three radially expandable cylinders 142, 144, 146 formed of wire in a zig-zag pattern. The diameter of minor cylinders 144, 146 is approximately half the diameter of major cylinder 142, and minor cylinders 144, 146 are mounted adjacent to one another at one end of major cylinder 142, so as to provide support for a branched vessel without obstructing fluid flow therethrough. The attachment of minor cylinders 144, 146 to major cylinder 142 may be by any suitable means, such as by forming a loop or hinge to provide a flexible joint, or by soldering the coils together.

Figure 13:
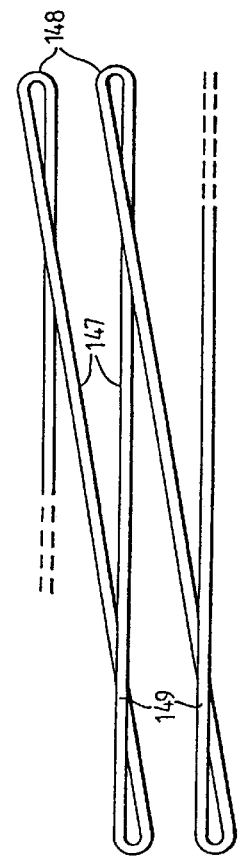
FIG. 13 is an enlarged view of two of the loops of the zig-zag stent of FIG. 12.

As best seen in FIG. 13, zig-zag stent 140 comprises a plurality of straight sections 147 joined by a series of loops 148, with a crossover 149 corresponding to each loop 148. The wire reverses directions at each loop 148, so that each straight section 116 crosses the two adjacent straight sections at cross-overs 149, forming a zig-zag pattern. A stent of this configuration has no longitudinal gap when expanded.

Stent 140 is radially expandable without thermal expansion or the application of torsional forces to the stent. The loops avoid sharp bends in the wire which might otherwise occur between adjacent straight sections, and, by enabling the straight wire sections to be crossed, increase the strength and stability of the stent. Additionally, zig-zag stent 140 can be constructed of a single, continuous piece of wire, with the wire passing form major cylinder 142 to each minor cylinder 144, 146 and back at least once.

Spiral Stent

Figure 14:
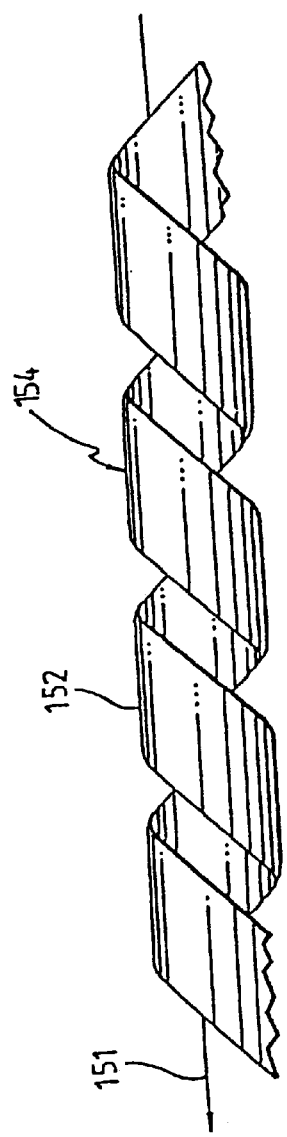
FIG. 14 is an isometric view of a nonbifurcated ribbon stent.
Figure 15:
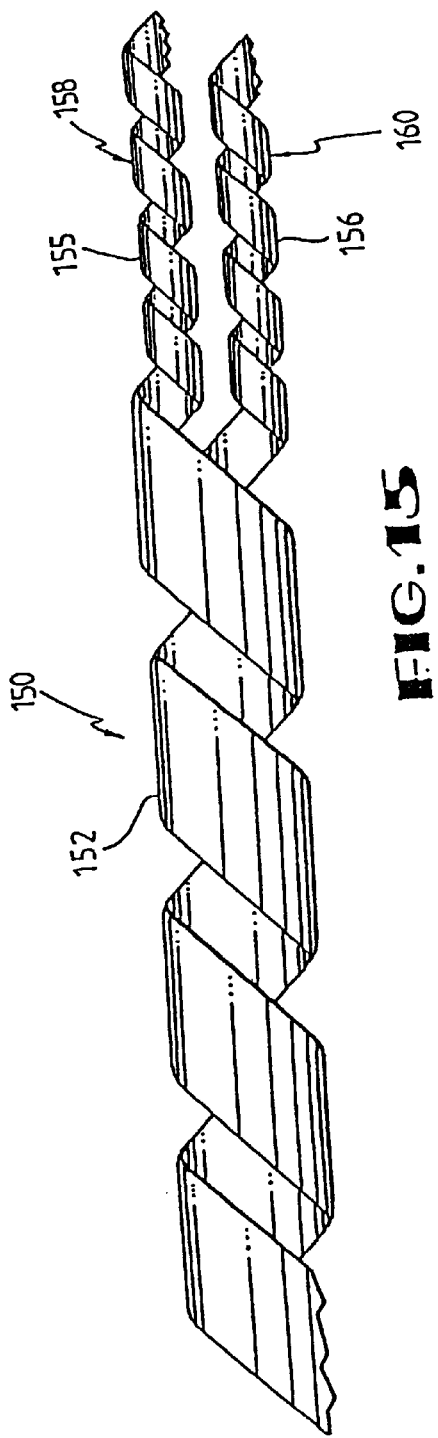
FIG. 15 is an isometric view of a bifurcated ribbon stent.

Referring now to FIGS. 14 and 15, an alternate embodiment of the present invention comprises a bifurcated stent 150 formed from a single, ribbon-like piece of material 152. The material used may be a solid strip of suitably deformable metal or plastic or other biocompatible substance, or it may be a mesh, such as of woven metal threads. To form a single coil 154, a strip of material having a desired width is wound around an axis 151. To form bifurcated stent 150, when the desired length of single coil 154 is attained, the remaining, uncoiled length of the strip is split lengthwise into two minor strips 155, 156, which are each coiled into a smaller but similar coil 158, 160.

It will be understood that a bifurcated stent may be constructed by combinations of the coil patterns disclosed herein other than the combinations shown in FIGS. 5 and 9. For example, the coil of FIG. 1, which is shown as a closed loop, could be opened and combined with two minor coils such as coils 83, 85. Such a combination would form a bifurcated stent from a single piece of wire with the wire ends terminating at the ends of the minor coils. These combinations do not depart from the spirit of the invention.

The advantages of a stent coiled according to the above description, and in particular a bifurcated stent, are discussed below. Primarily, the present coil is an improvement on the art because the relative stiffness of the regions of overlap and the turns are distributed longitudinally evenly about the axis of the coils. This is advantageous, as it is preferable that a stent not have a bias toward bending in one direction over another.

When a stent constructed according to the present invention is expanded into its supporting state, the outside diameter of the coil increased by decreasing the width of the regions of overlap. If the stent is expanded too much, the regions of overlap will disappear, as the intermeshed cusps will no longer overlap longitudinally. In the prior art this resulted in a longitudinal gap in the stent, across which the blood vessel was not supported. According to the present invention, even if the stent is expanded to such an extent that a gap is formed, the gap is helical, winding around the length of the stent. It is believed that a helical gap is preferable from a medical standpoint.

Because the stent of the present invention can be constructed from a continuous loop of wire, it eliminates the wire ends that are commonly present on the stents of the prior art. Such wire ends must be bent into loops, or otherwise treated, so as to decrease the likelihood of puncturing the vessel wall.

Double Spiral Stents

Figure 16:
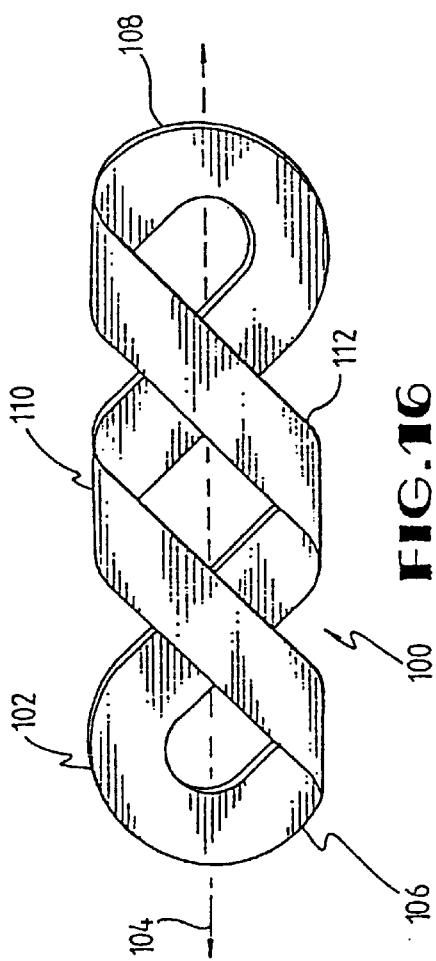
FIG. 16 is a perspective view of a double-spiral stent made according to the present invention.

Referring now to FIG. 16, a stent 100 having a double-spiral configuration, as opposed to a double-helix, is shown. As discussed above with respect to stent 10, stent 100 is preferably formed from a single continuous loop 102, such as that shown in FIG. 19 and discussed below. Loop 102 is twisted about an axis 104, such that a cylindrical coil having ends 106 and 108 and side sections 110 and 112 is formed. Each side section 110, 112 forms a spiral, with the two spirals being diametrically opposed except at ends 106, 108. Like stents 10 and 80, stent 100 provides uniform support around the circumference of a vessel. That is, it has no longitudinal gap. Unlike stents 10 and 80, however, stent 100 shortens or unwinds as it expands. This is a result of the spiral construction of, stent 100.

Figure 17:
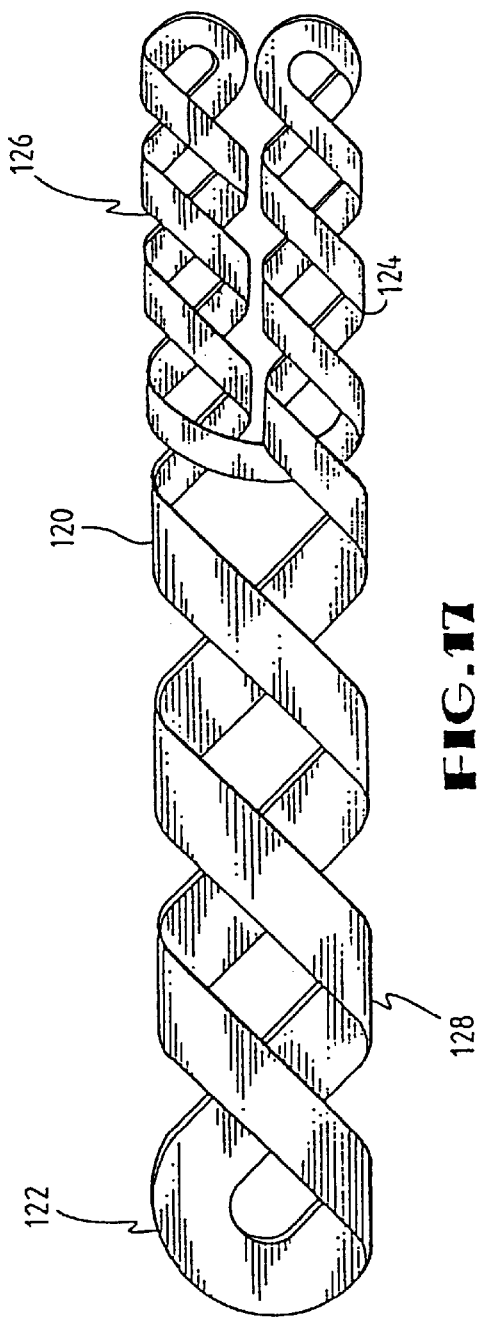
FIG. 17 is a perspective view of a bifurcated double-spiral stent made according to the present invention.

Again using spiral construction, a bifurcated stent 120, as shown in FIG. 17, may be formed. Bifurcated stent 120 includes a double-spiral major coil 122 and two double-spiral minor coils 124, 126. Stent 120 is preferably formed from a single continuous loop 128, and major coil 122 and minor coils 124, 126 are formed in the same manner as stent 100.

Figure 18:
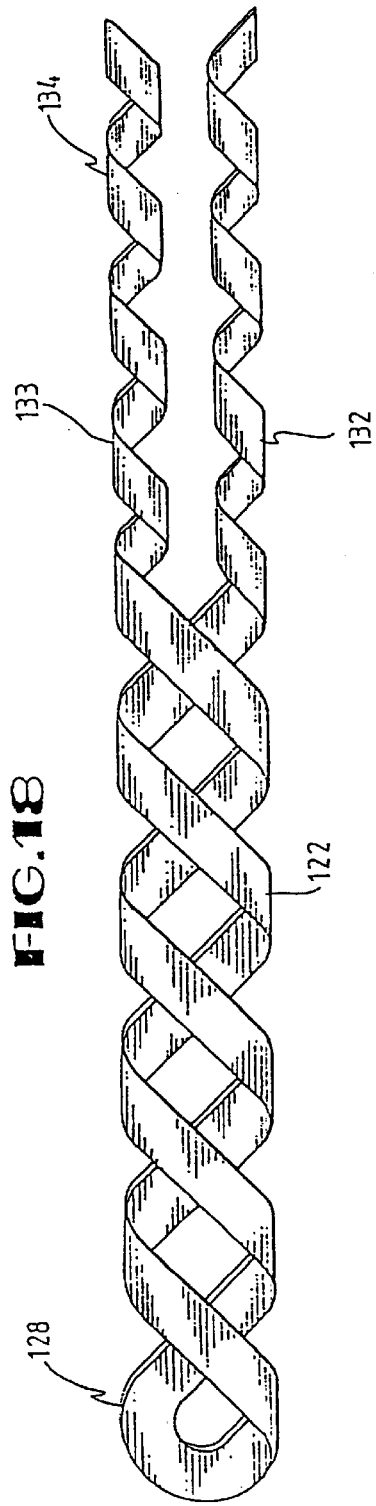
FIG. 18 is a perspective view of a bifurcated stent in which the major coil is a double-spiral and the minor coils are single spirals.

According to an alternate embodiment, shown in FIG. 18, loop 128 may be cut at one end of major coil 122, and the resulting ends 130, 132 may be individually coiled into single spirals. In this embodiment it is preferred that the exposed ends be looped back and connected to their respective coils in order to reduce the possibility of their puncturing the vessel in which they are installed, as at 134.

Methods of Making

According to the present invention, stents such as those described above are formed in a two-step process. The first step entails constructing a continuous loop, or blank, in the desired shape, while the second step entails forming the blank into a cylindrical coil. Methods for carrying out each step are described in detail below.

A. Forming a Continuous Loop or Blank

Figure 19A:
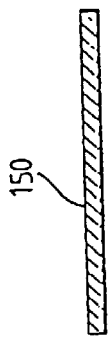
FIG. 19A is a cross section of the blank of FIG. 19 taken along lines A—A of FIG. 19.
Figure 19:
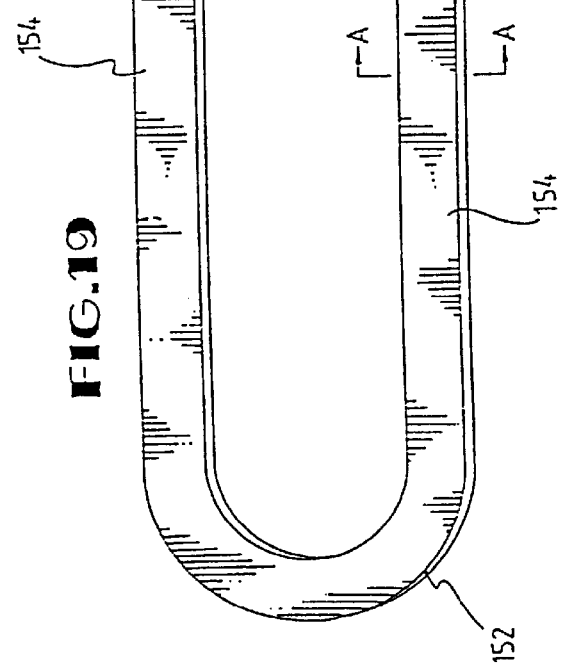
FIG. 19 is an perspective view of a continuous loop blank that may be used to form the stents of FIGS. 16 and 17.
Figure 20:
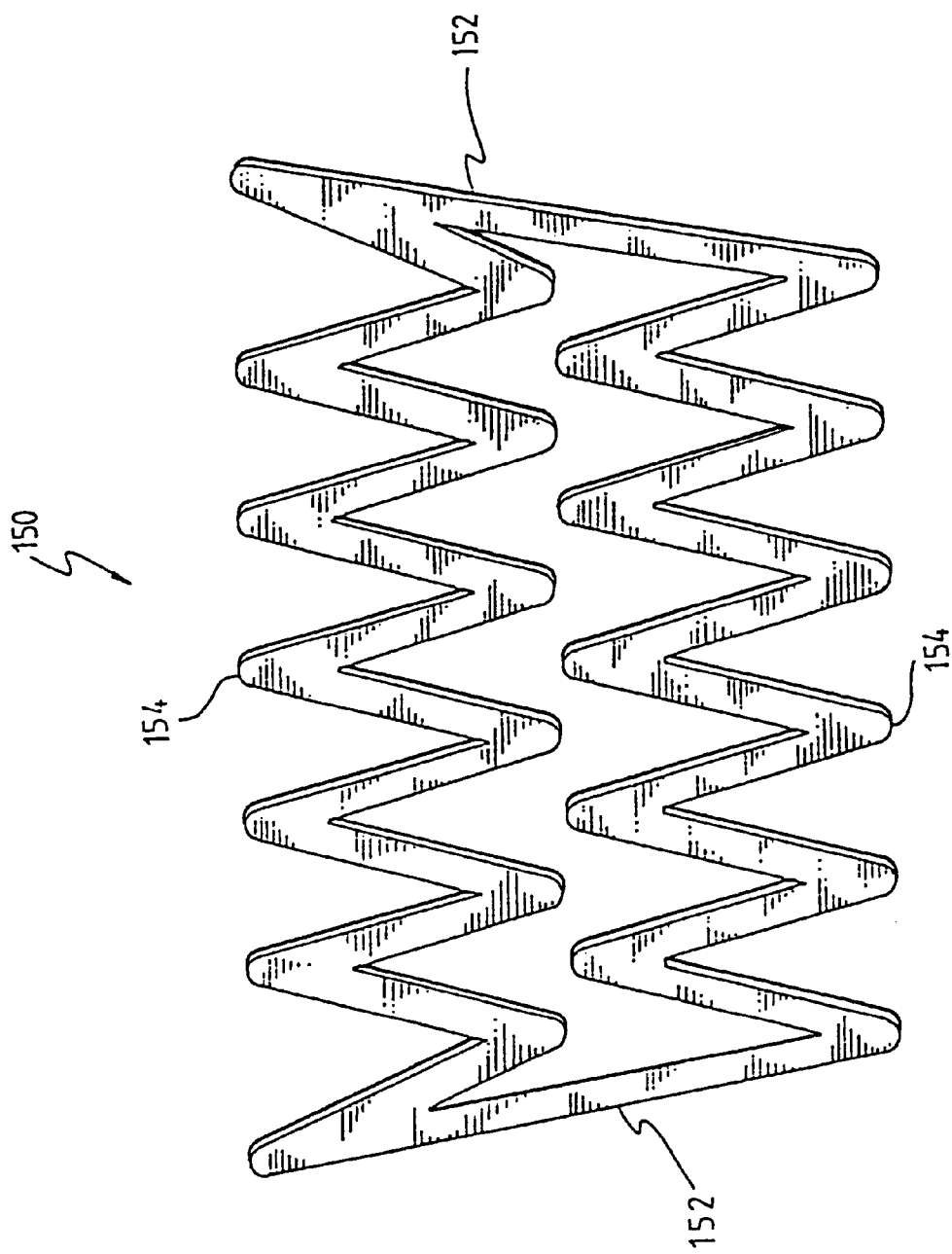
FIG. 20 is an elevational view of a continuous loop blank that may, be used to form the stents of FIGS. 1 and 6.

Continuous flat loops, or blanks, such as those shown in FIGS. 19 and 20, are preferably used to form the stents disclosed above. According to a preferred embodiment, each blank is formed by a photo-etching process. In this process, a drawing is made of the desired blank shape. The drawing is then reduced to actual size. The reduced drawing is used to produce a mask having the contours of the finished product. This mask is then affixed to the substance to be formed, preferably by means of an adhesive. The masked substance is exposed to an etching chemical, which causes those portions of the substance that are not covered by the mask to be dissolved. The etching chemical is preferably an acid-base substance, such as are widely available. The selection and strength of the etching chemical will be determined by the composition of the substance to be etched.

Alternatively, the blank may be formed by laser-etching a sheet of the substance out of which the stent is to be constructed. Laser-etching is a conventional cutting technique, the details of which are well-known in the art.

The substance that is etched can be any of various metals or metal alloys having the desired properties. For example, in some instances it may be preferable to use stainless steel in the manufacture of the stent, because of its strength and corrosion resistance. In other cases, a memory metal, such as Nitinol, may be used.

If a memory metal is used to form the stent, its shape-retaining properties can be used to advantage in two ways. First, if a stent in the austenitic condition is formed into the desired stent shape and allowed to cool into martensite, it can be compressed or collapsed for deployment. Collapsing of the stent deforms the martensite, which retains the collapsed shape. The collapsed stent can be deployed and then expanded by a brief application of heat, thereby obviating the need for a balloon. This would be particularly advantageous in instances where it is desirable to deploy and expand a bifurcated stent, as it avoids the need to position and then remove a Y-shaped balloon.

The second useful application of memory metals in vascular support is where it is desired to expand a vessel whose diameter has decreased to an unsafe degree. In these instances an austenitic stent is preformed such that it has a diameter slightly greater than that of the collapsed vessel into which it is to be deployed. The material is selected so that it is "super-elastic" in the temperature range of the human body. Because the material is therefore springy and can be subjected to significant stress without deformation, the stent can be collapsed and deployed without the use of heat. Because the material does not deform during collapse, it must be contained in a catheter that is capable of resisting the expansive spring force of the stent. Once deployed because the diameter of the stent is larger than the vessel diameter, the stent exerts a dilative radial force on the vessel wall. This causes the vessel to expand until the stent is fully expanded. This would eliminate the present need to use balloons to expand a collapsed vessels and/or collapsed stents.

Once etching is complete, the mask is removed, leaving only the cleanly cut metal blank 150, as shown in FIGS. 19 and 20. Each blank includes a pair of ends 152 and a pair of legs 154 extending between ends 152. Because the starting material for the mask typically comprises a flat sheet, mask 150 will have a rectangular cross-section, as shown in FIG. 19A. The thickness of the sheet of starting material will determine the thickness of blank 150.

It will be noted that the legs 154 of blank 150 shown FIG. 19 are essentially straight, except where they curve together at ends 152. In contrast, each leg 154 of blank 150 of FIG.20 is cut into an inclined, serpentine shape. Each serpentine leg forms cusps 155, which are designed to intermesh when the blank is formed into a cylindrical coil.

Figure 21:
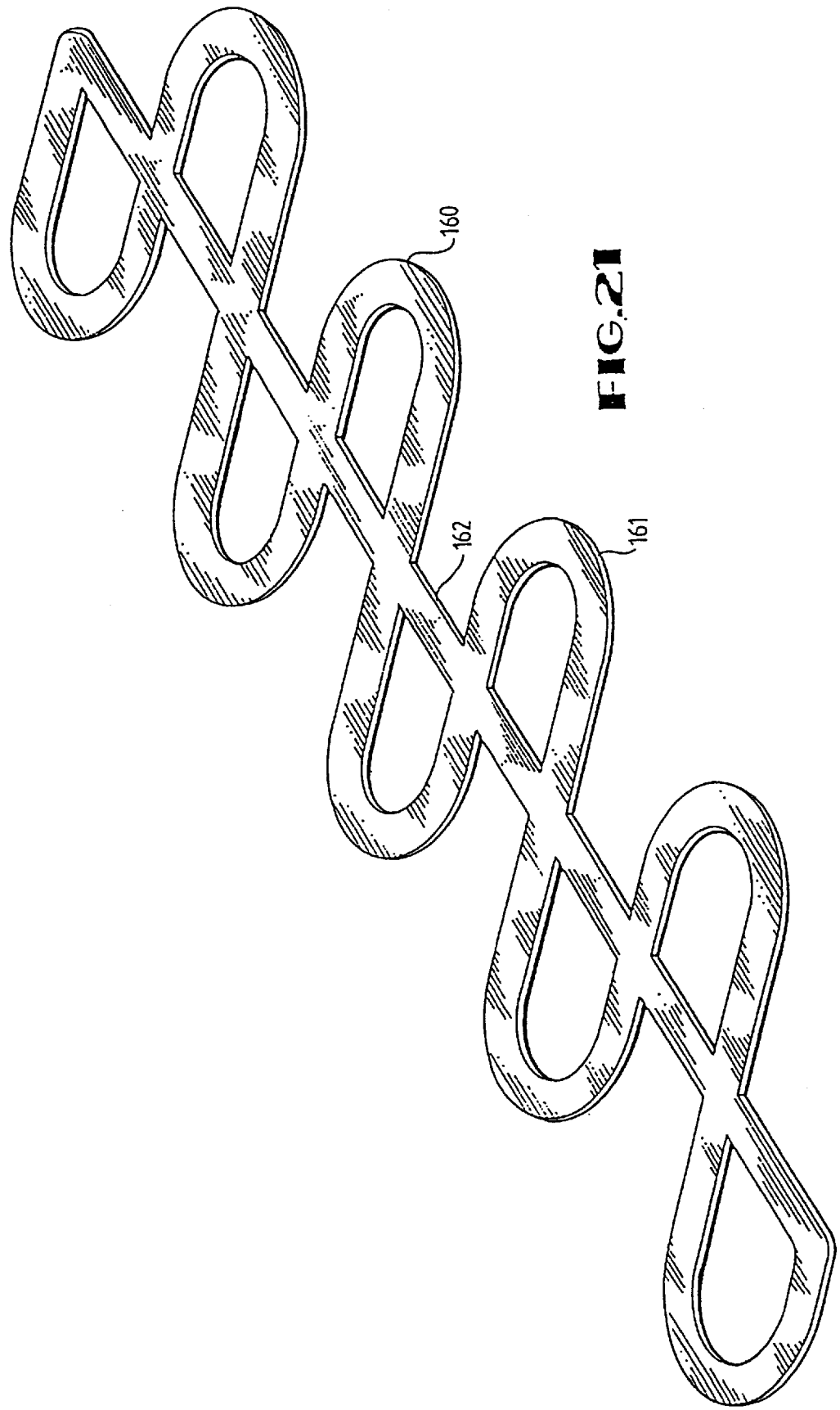
FIG. 21 is a perspective view of a backbone blank.

Still another type of blank that can be etched and formed according to the present invention is the rib-cage blank 160 shown in FIG. 21. This blank includes a longitudinal spine 162 with a plurality of looped ribs 164 extending therefrom. Ribs 164 are preferably substantially U-shaped, as shown, in order to minimize turbulence in the fluid passing through the stented vessel, to maximize conformability of the stent to the interior of the vessel, and to minimize the likelihood of a puncture.

Other methods for forming a continuous blank may alternatively be employed. For example, two ends of a piece of wire may, be soldered or welded and then machined to produce a smooth coupling. However these methods for forming are less desired because they require additional manufacturing steps and do not produce an integral piece as does photoetching.

B. Coiling the Blank into a Stent

Once blank 150 has been formed, it is shaped into its ultimate cylindrical form by one of the following methods.

Figure 22:
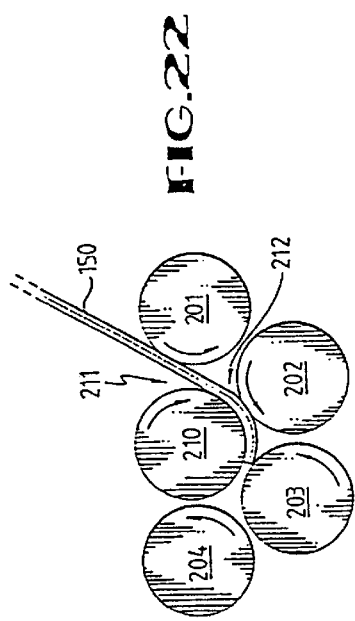
FIG. 22 is an end view of an apparatus that can be used according to the present invention to produce the stents of FIGS. 1, 5, 6, 7, 16, 17, and 21.
Figure 24:
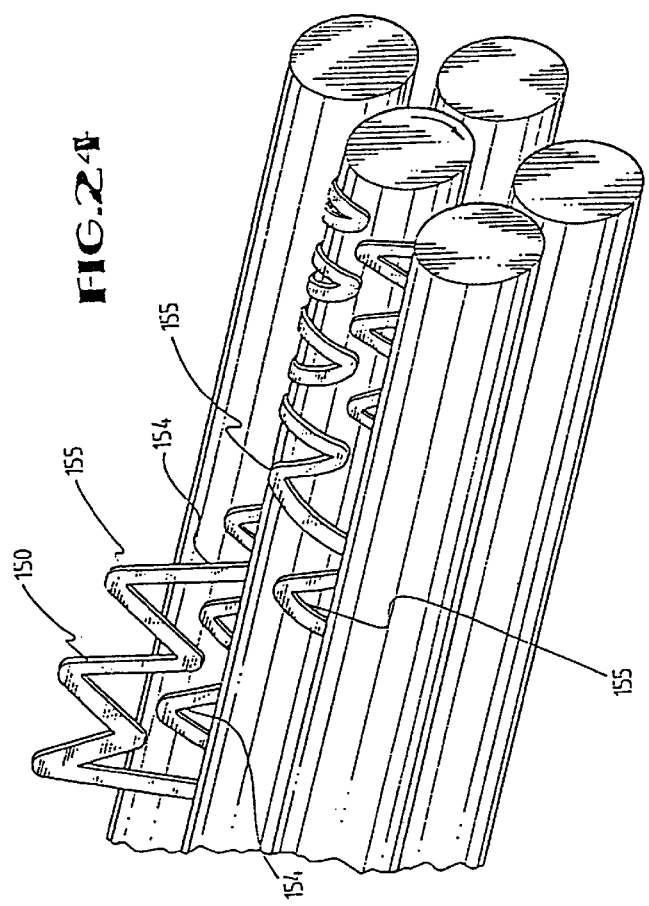
FIG. 24 is a perspective view of the apparatus of FIG. 22 forming the loop of FIG. 20 into the stent of FIG. 1.

Preferably, a plurality of secondary rollers 201–204 may be used as shown in FIG. 22 to wrap blank 150 around a drive roller or mandril 210. Secondary rollers 201–204 are positioned so that they do not contact each other and are spaced slightly apart from and parallel to drive roller 210. The space between each secondary roller 201–204 and drive roller 210 is preferably equal to or slightly less than the thickness of blank 150.

As shown in FIG. 22, blank 150 is fed at a steady rate into the gap 211 between the first secondary roller 201 and drive roller 210. The rotating surfaces of these two rollers propel blank 150 toward the succeeding gap 212 between secondary roller 202 and drive roller 210. The rotating surfaces of these two rollers in turn propel blank 150 toward succeeding gap 213. In this manner, blank 150 is propelled completely around drive roller 210. The passage of blank 150 around one circumference of roller 210 results in blank 150 assuming a cylindrical shape.

Figure 23:
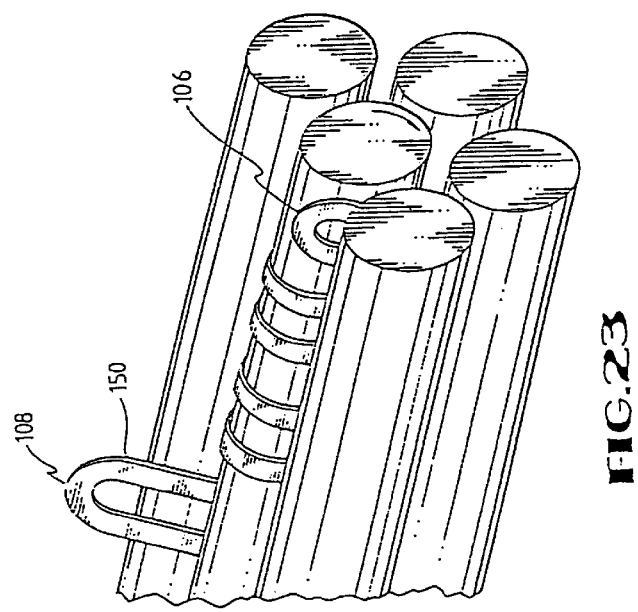
FIG. 23 is a perspective view of the apparatus of FIG. 22 forming the loop of FIG. 19 into the stent of FIG. 16.

If blank 150 is fed at an oblique angle with respect to the axis of drive roller 210, as shown in FIG. 23, the opposite edges or sides of blank 150 and the gap defined therebetween will form a longitudinal spiral around the drive roller. If a blank having straight sides is used, such as is shown in FIG. 19, a double-spiral stent like that shown in FIG. 16 will be formed. If, however, a serpentine blank is used, such as is shown in FIG. 20, a double helix stent like that shown in FIG. 1 will be formed. The positioning of cusps 155 of each leg 154 with respect to cusps 155 of the other leg 154 will determine the pattern of circumferential support provided by the stent to the vessel. It has been found that an slanted serpentine blank like that of FIG. 20 will produce the desired double helix stent in which the longitudinal gap or region of overlap between the cusps defines a spiral around the stent.

Figure 25:
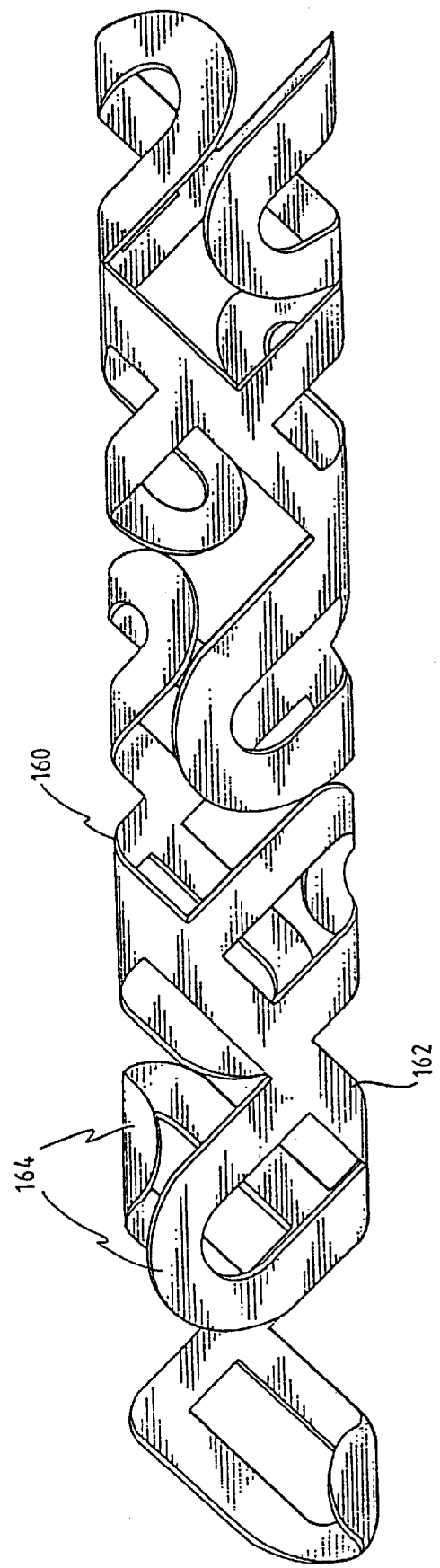
FIG. 25 is a perspective view of a stent formed from the rib-cage blank of FIG. 21.

As above, rib-cage blank 160 may also be fed into the rolling mechanism to be formed into a cylindrical shape. Referring now to FIG. 25, if blank 160 is fed into the rollers obliquely, spine 162 will describe a spiral and ribs 164 will intermesh to more completely define the desired cylindrical shape. Alternatively, blank 160 may be formed into the desired shape by other mechanical means.

It will be recognized by one skilled in the art that the foregoing method is superior to prior methods of forming a complex stent such as the double-helix stent in that the present method allows rapid, consistent, and symmetrical assembly of the desired shape and is not labor intensive. If, however, the necessary equipment is unavailable, the stents disclosed above may be formed "by hand," such as by manually wrapping or pulling the blank into shape around a mandril.

While the foregoing stents described may be used alone, particularly if they are coated with a biocompatibilized gel as described above, it may optionally be desired to provide a casing for the deployed stent. Such a casing, or graft as they are called, may comprise a tube-shaped member having an inside diameter only slightly larger than the circumference of the deployed stent. The casing may be made of latex, silicone latex, polytetraflouroethylene, polyethylene, dacron polyesters, polyurethane or other suitable biocompatible material. The graft material must be flexible and durable, so that it can withstand the effects of installation and usage. Depending on the material chosen, it may be preferable to form the graft in one of several ways. For example, the graft may be extruded, woven or formed by dipping a substrate in the desired material, removing the material from the substrate, and trimming the end of the material, so as to form a cylindrical tube having an opening at each end.

The graft is deployed simultaneously with the deployment of the stent. Prior to deployment, the graft is collapsed, with the collapsed stent inside it. As described, the stent and craft may then be inserted into a catheter, deployed, and expanded by pressurization of a balloon. A graft deployed and supported in this manner may be used to seal an aneurysm or similar defect in a vessel. The tissue of the vessel adjacent to the graft will grow onto the graft, so that the graft becomes an integral, reinforcing that part of the vessel wall and helping to reduce the risk of future ruptures at that location.

While a preferred embodiment of the invention has been shown and described, modifications thereof can be made by one skilled in the art without departing from the spirit of the invention. It will further be understood that stents according to the present invention may be used in other body passageways, such as the urinary, biliary, or esophageal tract, with construction and deployment of the stents being essentially as described above.

What is claimed is:

1. A method for making a stent having a first, radially compressed position and a second, radially expanded position, comprising the steps of:
    forming a continuous closed-loop blank, said continuous closed-loop blank comprising two legs, each of said legs having first and second ends, said first leg ends being joined at a first stent end and said second leg ends being joined a second stent end, said legs being serpentine between said ends, and
    wrapping the blank helically around a mandrel so as to form a cylindrical coil in which the blank does not cross itself, the coil being configured such that when the stent is in its radially compressed position the arcuate ribs formed by the serpentine legs overlap each other circumferentially.

2. The method according to claim 1, further including the step of forming the blank by photoetching.

3. The method according to claim 1, further including the step of forming the blank by laser etching.

4. The method according to claim 1, further including the step of forming the blank from a memory metal.

5. The method according to claim 1, wherein said wrapping step includes passing the blank between the mandrel and a plurality of secondary rollers.

6. A method for making a stent, comprising the steps of:
    forming a blank, the blank including a longitudinal spine and a plurality of looped U-shaped ribs extending transversely from the spine, and
    wrapping the blank helically around a mandrel so as to form a cylindrical coil that does not cross itself and in which the transversely extending U-shaped ribs overlap circumferentially.

7. The method according to claim 6, further including the step of forming the blank by photoetching.

8. The method according to claim 6, further including the step of forming the blank by laser etching.

9. The method according to claim 6, further including the step of forming the blank from a memory metal.

10. The method according to claim 6 wherein said wrapping step includes passing the blank between the mandrel and a plurality of secondary rollers.

* * * * *